(12) United States Patent
Scanlin et al.

(10) Patent No.: US 7,563,473 B2
(45) Date of Patent: Jul. 21, 2009

(54) QUINOA PROTEIN CONCENTRATE, PRODUCTION AND FUNCTIONALITY

(75) Inventors: Laurie Scanlin, Arvada, CO (US); Martha Stone, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 141 days.

(21) Appl. No.: 10/596,259

(22) PCT Filed: Dec. 16, 2004

(86) PCT No.: PCT/US2004/042296

§ 371 (c)(1), (2), (4) Date: Sep. 20, 2006

(87) PCT Pub. No.: WO2005/058249

PCT Pub. Date: Jun. 30, 2005

(65) Prior Publication Data

US 2007/0092629 A1   Apr. 26, 2007

Related U.S. Application Data

(60) Provisional application No. 60/530,219, filed on Dec. 16, 2003.

(51) Int. Cl.
*A23J 1/00* (2006.01)
*A23J 1/14* (2006.01)
*A23L 1/20* (2006.01)
*A23L 1/212* (2006.01)
*A23L 1/214* (2006.01)

(52) U.S. Cl. .............. 426/656; 426/661; 426/615; 426/629; 426/478; 426/481; 426/484; 426/506; 426/507; 426/518; 426/519; 426/425

(58) Field of Classification Search ............. 260/112; 426/629, 425, 506, 507, 518, 519, 478, 481, 426/484, 656, 661, 615
See application file for complete search history.

(56) References Cited

U.S. PATENT DOCUMENTS

| | | | |
|---|---|---|---|
| 4,072,666 A * | 2/1978 | Horisberger et al. | 530/379 |
| 4,175,075 A * | 11/1979 | Garrison et al. | 530/377 |
| 4,677,065 A | 6/1987 | Buchbjerg et al. | |
| 4,716,218 A | 12/1987 | Chen et al. | |
| 4,911,943 A * | 3/1990 | Slimak | 426/629 |
| 5,034,227 A | 7/1991 | Nickel | |
| 5,264,231 A | 11/1993 | Thomas | |
| 5,410,021 A | 4/1995 | Kampen | |
| 6,261,629 B1 | 7/2001 | Mazza et al. | |
| 6,936,110 B2 | 8/2005 | Van Thorre | |
| 2004/0214300 A1 | 10/2004 | Wasche et al. | |

FOREIGN PATENT DOCUMENTS

| | | |
|---|---|---|
| CN | 1589664 | 3/1995 |
| EP | 0593292 | 4/1994 |
| WO | 8912403 | 12/1989 |
| WO | WO 89/12403 | 12/1989 |
| WO | 9622027 | 7/1996 |

OTHER PUBLICATIONS

Supplementary European Search Report, EP Application No. 04 81 4475, Jan. 9, 2008, 5 pages.
N. Thoufeek Ahamed et al., Physicochemical and functional properties of *Chenopodium quinoa* starch, Carbohydrate Polymers 31:99-103, 1996.
L. Coulter et al., "Quinoa—Composition, nutritional value, food applications," Lebensmittel Wissenschaft and Technologie 23(3):203-207, 1990.
R. Gross et al., "Chemical composition and protein quality of some local Andean food sources," Food Chemistry 34:25-34, 1989.
K. Lorenz, "Quinoa (*Chenopodium quinoa*) starch—physico-chemical properties and functional characteristics," Starch 42(3):81-86, 1990.
R. Przybylski et al., "Characterization of quinoa (*Chenopodium quinoa*) lipids," Food Chemistry 51:187-192, 1994.
S. G. Wood et al., "Seed lipid content and fatty acid composition of three quinoa cultivars," Journal of Food Composition and Analysis 6:41-44, 1993.
R. E. Aluko et al., Functional and bioactive properties of Quinoa seed protein hydrolysates, Journal of Food Science 68 (4):1254-1258, 2003.

(Continued)

*Primary Examiner*—Jon P Weber
*Assistant Examiner*—Marsha M Tsay
(74) *Attorney, Agent, or Firm*—Michael M. McGaw; Smith and Hopen, P.A.

(57) ABSTRACT

The present invention relates to a new source of high quality plant protein, termed, "*quinoa* protein concentrate (QPC)", which contains at least about 50 wt % protein which is food-grade and/or pharmaceutical-grade and methods of preparing such protein concentrates as well as starch, oil, and fiber from *quinoa* grain. The *quinoa* protein concentrate of the invention is useful as food ingredients, infant formula ingredients, cosmetic ingredients, pet food ingredients, and animal feed supplements.

18 Claims, No Drawings

OTHER PUBLICATIONS

G. S. Chauhan et al. Effect of saponin extraction on the nutritional quality of Quinoa (*Chenopodium quinoa* Willd.) proteins, Journal Food Science Technology 36(2):123-126, 1999.

G. S. Chauhan et al., Effect of saponin on the surface properties of quinoa proteins, International Journal of Food Properties 2(1):13-22, 1999.

International Search Report, International Application No. PCT/US04/42296, Jul. 27, 2006, 4 pages.

O. Hiroshi et al., Effect of quinoa on blood pressure and lipid metabolism in diet-induced hyperlipidemic spontaneously hypertensive rats (SHR), Journal of Japanese Society of Nutrition and Food Science 54(4):221-227, 2001, abstract only.

G. S. Ranhotra et al., Composition and protein nutritional quality of quinoa, Cereal Chemistry 70(3):303-305, 1993.

G. S. Chauhan et al., Nutrients and antinutrients in quinoa seed, Cereal Chemistry 69(1):85-88, 1992.

K. H. Wright et al., Isolation and characterization of atriplex hortensis and sweet chenopodium, Cereal Chemistry 79(5):715-719, 2002, abstract only.

T. Karyotis et al., Preliminary research on seed production and nutrient content for certain quinoa varieties in a saline-sodic soil., Journal Agronomy and Crop Science 189:402-208, 2003.

Aluko R.E. et al. "Functional and bioactive prperties of Quinoa Seed protein hydrolysates." Journal of Food Science. vol. 68, No. 4. 2003. pp. 1254-1258.

Chauhan G.S. et al. "Effect of saponin on the surface properties of quinoa proteins." IFIS. Database FSTA No. 199-00-m0659, 1999.

Przybylski et al. "Characterization of quinoa (*Chenopodium qunioa*) lipids." Food Chemistry. Elsevier Science Publishers LTD. G.B. vol. 51. 1994. pp. 187-192.

Wood S.G. et al. "Seed lipid content and fatty acid composition of three quinoa cultivars." Journal of Food Composition and Analysis. vol. 6, No. 1. 1993. pp. 41.

Ahamed N. T. et al. "Physicochemical and functional properties of *Chenopodium quinoa* starch." Carbohydrate Polymers. Applied Science Publishers, LTD. Barking, G.B. vol. 31. No. 1. Sep. 1996. pp. 99-103.

Wright K.H. et al. "Isolation and chararcterization of *Atriplex hortensis* and sweet *Chenopodium quinoa* starches." Cereal Chemistry. vol. 79. No. 5. 2002. pp. 715-719.

Lorenz K. "Quinoa (*Chenopodium quinoa*) Starch-Physicochemical Properties and Functional Characteristics Quinoa (*Chenopodium quinoa*) Staerke-Physikalisch-Chemische Eigenschaften Und Funktionalla Charakteristika" Starke-Starch, Wiley-Vch Verlag, Weinheim, DE. vol. 42. No. 3. 1990. pp. 81-86.

\* cited by examiner

QUINOA PROTEIN CONCENTRATE, PRODUCTION AND FUNCTIONALITY

CROSS REFERENCE TO RELATED APPLICATIONS

This application is the National Stage of International Application No. PCT/US2004/042296, filed Dec. 16, 2004, which claims priority to U.S. Provisional Patent Application Ser. No. 60/530,219, entitled, "*Quinoa* Protein Concentrate, Production and Functionality", filed Dec. 16, 2003, the contents of which applications are herein incorporated by reference.

FIELD OF INVENTION

The present invention relates to a *quinoa* protein concentrate containing at least about 50 wt % protein and a method of processing *quinoa* (Genus: *Chenopodium*, Species: *quinoa*, Family: Chenopodiaceae) grain (also called *quinoa* seed, quinua, grain-like seed, pseudocereal, and fruit) to produce such protein concentrate, oil, starch, and fiber.

BACKGROUND OF THE INVENTION

Plant proteins, processed from cereal grains and legumes, are profitable ingredients in a wide variety of commercial food products, pet foods, and animal feed. Examples of the plant proteins that are currently available are soy protein concentrate, isolated soy protein, wheat gluten, rice, and corn proteins [Food Master (2003) Ingredients and R&D services catalog. Bensenville Ill. Business News Publishing Co. II. LLC].

However, plant proteins are often limiting in one or more essential amino acids. For example, the plant proteins of wheat, rice and corn are limiting in lysine [Hoseney, R C (1986) In: Principles of cereal science and technology. St. Paul, Minn.: American Association of Cereal Chemists, Inc. ppg. 69-88], whereas, soy protein is limiting in methionine and cystine [Haard and Chism (1996) In: Fennema Oreg., editor. Food Chemistry, $3^{rd}$ ed. revised and expanded. New York: Marcel Dekker, ppg. 943-1011]. Though, well processed isolated soy proteins and soy protein concentrates have been found to be equivalent to animal protein in regard to the needs of human nutrition [Young, V R (1991) *J. Am. Diet Assoc.* 7: ppg. 828-835].

Yet, the following eight foods that are a good source of animal or plant protein account for 90% of all food allergenic reactions: soy, wheat, eggs, milk, peanut, treenut, fish and shellfish [Hefle, S. L. et al. (1996) Crit. Rev. Food Sci. Nutr. 36(5): ppg. 69-89]. Food allergens are a serious concern because essential nutrients for proper health can be missing with a narrowed food choice, in addition to the life-threatening concern of anaphylactic shock in highly sensitive individuals. Allergens are problematic for food producers because many food ingredients fall into this category and limit product development. The impact that food allergens, including undeclared food allergens, have had on the food industry is remarkable and the FDA has stated that food allergens are a top priority this year [Hefle, S. (Sep. 2003) Symposium: Update on Food Allergens. American Association of Cereal Chemists Annual Meeting. Portland, Oreg.].

As world food demands steadily increase, production of protein has to be maximized, as well as augmented. Plant proteins from cereals and legumes represent the main source of proteins and energy supply for both human and animal nutrition. This is partly due to the fact that animal proteins require much higher energy demand for production and are therefore more expensive to produce than plant proteins [Cheftel, J C et al. (1985) In: Fennema Oreg., editor. Food Chemistry, $2^{nd}$ ed. New York: Marcel Dekker. ppg. 245-369]. For example, in order to produce 1 kg of animal protein, 3-20 kg of plant protein is needed. Consequently, as demands for animal protein increase globally, the need for plant protein increases drastically. To meet this need, new protein resources must be developed. Protein-rich crops that give equitable yields in underutilized growing regions are of paramount value for this purpose. Alternatively, new crops can be selected and tested for a protein source.

Since 1975, *quinoa* has become an alternative crop in North America and Europe for the following reasons [Fleming and Galwey (1995) In: Williams, J T, editor. Underutilized Crops: Cereals and Pseudocereals. New York: Chapman and Hall, ppg. 3-83]; *quinoa* has the ability to thrive in marginal soils, where traditional crops cannot, therefore, underutilized growing regions can be cultivated; *quinoa* has an average protein content of 14.6%, which is higher than traditional cereals, with certain varieties containing protein levels as high as 21.9%; and *quinoa* has an amino acid composition, protein efficiency ratio, protein digestibility, and nitrogen balance comparable to milk protein, casein. Consequently, it is rare for a plant protein to so closely resemble that of animal origin.

*Quinoa* protein is particularly high in lysine and methionine, amino acids limiting in cereal grains and legumes, respectively [Koziol, M J (1992) *J. Food Composition and Analysis* 5: ppg. 35-68]. *Quinoa* protein is also high in histidine, an essential amino acid for infant development and those with chronic diseases [Ettinger, S (2000) In: Mahan K L, Escott-Stump S, eds. Krause's Food, Nutrition, and Diet Therapy, $10^{th}$ ed. Philadelphia, Pa. WB Saunders Co. ppg. 54-61]. In South America, it has been used as a weaning food for centuries because of its nutritional attributes and high protein digestibility.

Additionally, *quinoa* is not on the list of recognized food allergens. It is considered free of gluten or prolamins [Fairbanks, D J et al. (1990) *Plant Breeding* 104(3): ppg. 190-195], the protein associated with allergenic reactions in wheat gluten, rye and barley. Prolamins, like gliadins found in wheat, ignite immune responses in patients with gluten-induced enteropathy, also known as celiac disease. *Quinoa* is a pseudocereal named for its production of small grain-like seeds, although the actual harvested grain is a single seeded fruit [Shewry, P R (2002) In: Belton P S, Taylor J. eds. Pseudocereals and Less Common Cereals. Germany: Springer-Verlag Berlin Heidelberg. ppg. 93-122]. It is a dicotyledonous species not closely related to the monocotyledonous species of true cereal grains like wheat, rye, and barley. As a result of differences in plant taxonomy, *quinoa* does not contain the harmful amino acid sequences found in wheat. Therefore, it is concluded safe for a gluten-free diet [Thompson, T. (2001) J. Am. Diet. Assoc. 101: ppg. 586-587] and is recommended by the Celiac Disease Foundation and Gluten Intolerance Group. Furthermore, research presented at the International Workshop on Food Supplementation in Food Allergy and Immunity, found that *quinoa* is immunochemically safe and represents a viable alternative for gluten-free products [Berti, C et al. (Aug. 2002) International Workshop on Food Supplementation in Food Allergy and Immunity. Olsztyn].

Despite the numerous beneficial properties of *quinoa* as a plant protein source as described above, *quinoa* grain has not been processed efficiently to extract individual components contained therein. Currently, *quinoa* is available only as whole grain or ground for a small number of products. Therefore, there is a need in the art to develop a method to process *quinoa* grains into individual components, i.e., protein, oil, fiber, and starch, which are food-grade and/or pharmaceutical-grade that can readily be utilized as nutritional supplements as well as agents for providing functionality in a variety of food products, cosmetic products, and animal feeds. The present invention meets this need. The advantage of the invention will be evident in the following description.

BRIEF SUMMARY OF THE INVENTION

The present invention provides a new source of plant protein, termed "*quinoa* protein concentrate (QPC)", prepared from *quinoa* (*Chenopodium quinoa* Chenopodiaceae) grain, which contains at least about 50 wt % protein, preferably at least about 70 wt % protein, most preferably at least about 90 wt % protein, on a dry weight basis. The QPC of the invention is high in lysine and histidine, and methionine and cystine, which are often limiting in plant proteins of grains and legumes, respectively. Additionally, *quinoa* is considered to be hypo-allergenic (even non-allergenic), as opposed to key plant allergens, soy and wheat. Therefore, the *quinoa* protein concentrate is useful as food ingredients and supplements to provide nutrients as well as necessary functionality in a variety of food products including infant formula, pet foods and animal feeds. For example, the QPC can be added in a variety of products such as foods for infants and toddlers, meat analogs, ice creams, whipped toppings, baked products, and salad dressings and the like, to reduce water activity, reduce fat, bind ingredients, emulsify, and/or stabilize foams. The QPC of the invention are particularly useful as an ingredient to fortify the amino acid composition of corn- or rice-based food products, which are also considered to be hypo-allergenic, but are either low in protein content or limiting in essential amino acid, lysine. The QPC can be used as a protein source in food or cosmetic products intended for use in subjects who require less- or hypo-allergenic food products. In addition, QPC can serve as a high quality, plant protein in pet foods and animal feeds like cattle feed, since the FDA banned the use of animal protein in cattle feed as a preventative measure against bovine spongiform encephalopathy (i.e., BSE or mad cow disease) [DEPARTMENT OF HEALTH AND HUMAN SERVICES (2004), Food and Drug Administration, 21 CFR Parts 189 and 700, [Ser. No. 10/688773, Use of Materials Derived From Cattle in Human Food and Cosmetics].

Also provided is a process for isolating individual components contained in quinoa (*Chenopodium quinoa* Chenopodiaceae) grain such as protein (termed QPC herein), oil, starch, and fiber. The process comprises the steps of; 1) flaking or comminuting *quinoa* grain, 2) extracting oil from the flaked or comminuted *quinoa* grain leaving defatted *quinoa*, 3) extracting protein from the defatted *quinoa* in alkaline solution, 4) separating the fraction containing the protein from the mixture, and 5) drying the solubilized protein, whereby a *quinoa* protein concentrate containing at least about 50 wt % protein is obtained. The term, "comminution" or "comminuting", is generically used herein to indicate a step of treatment such as grinding, milling, disintegration, trituration, pulverization, etc. *Quinoa* oil, fiber, and starch can be readily obtained from this process by employing simple manipulations such as separation or concentration, which are well known in the art. It will be understood by those skilled in the art that the process disclosed herein can be operated with appropriate modifications and variations to obtain the aforementioned products. For example, the *quinoa* grain can be mechanically abraded prior to the step of comminution and/or the *quinoa* grain can be shaped (such as flaked) prior to the step of comminution, and/or the *quinoa* grain can be conditioned (such as tempered) prior to the step of comminution. The protein fraction obtained after step (4) can be further purified by isoelectric precipitation before step (5), if necessary. The process disclosed herein is designed to maximize isolation of the individual components contained, in *quinoa* grain and thus enables one to obtain other components such as *quinoa* oil, starch, and fiber at different stages of the process, as illustrated in the flow diagrams below.

DETAILED DESCRIPTION OF THE INVENTION

In general the terms and phrases used herein have their art-recognized meaning, which can be found by reference to standard texts, journal references and contexts known to those skilled in the art. The following definitions are provided to clarify their specific use in the context of the invention.

The term, "*quinoa* protein concentrate (QPC)", as used herein, is intended to indicate the product obtained from *quinoa* (Genus: *Chenopodium*, Species: *quinoa*, Family: Chenopodiaceae) grain (also called *quinoa* seed, grain-like seed, pseudocereal, and fruit) having a protein content of at least about 50 wt %, preferably of at least about 70 wt %, most preferably of at least about 90 wt %, on a dry weight basis, and is food- and pharmaceutical-grade. The QPC can be obtained by the processes disclosed herein with or without modifications. The protein content is determined by the procedure as described in American Association of Cereal Chemists: "Approved Methods of Analysis," The Association, St. Paul, Minn., 2000. However, any art-recognized methods can be used to determine the protein content in the product obtained by the process of the invention. Typically, the percentage of the protein content on a dry weight basis is determined by kjeldahl nitrogen×6.25 (N×6.25).

The term, "functionality", is a well known term in the food industry and relates to physical and chemical properties of food molecules that affect their behavior and produce desired effects in foods during formulation, processing, preparation, and storage [Murano, PS (2003) Understanding Food Science and Technology. Belmont, Calif.: Wadsworth/Thomson Learning, Inc.]

The term, "infant food", more commonly referred to as "food for infants" means any food product intended for use for infants up to one year in age, and generally refers to solid foods for older infants age six months to one year in age. "Foods for toddlers" generally refers to foods for toddlers age one year to two year in age. "Foods for children" refers to foods for pre-school children age 2-5 years and schoolchildren up to 12 years in age. The designation becomes important when estimating amino acid requirements.

When a Markush group or other grouping is used herein, all individual members of the group and all combinations and subcombinations possible of the group are intended to be individually included in the disclosure. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Disclosed herein is a new plant protein source termed, *quinoa* protein concentrate, having a protein content of at least about 50 wt % on a dry weight basis, and other isolated components contained in *quinoa* (*Chenopodium quinoa* Chenopodiaceae) grain. Despite the recent interest in *quinoa* in the food, paper, and cosmetic industries due to its unique starch properties and high lipid content compared to other cereals, *quinoa* as a plant protein source has not been explored. The inventors herein discovered an efficient process by which maximum amounts of quinoa protein, as well as other isolated components of commercial value such as oil, fiber, and starch contained therein, can be obtained.

Exemplified below are three schemes by which the process of the invention can be practiced.

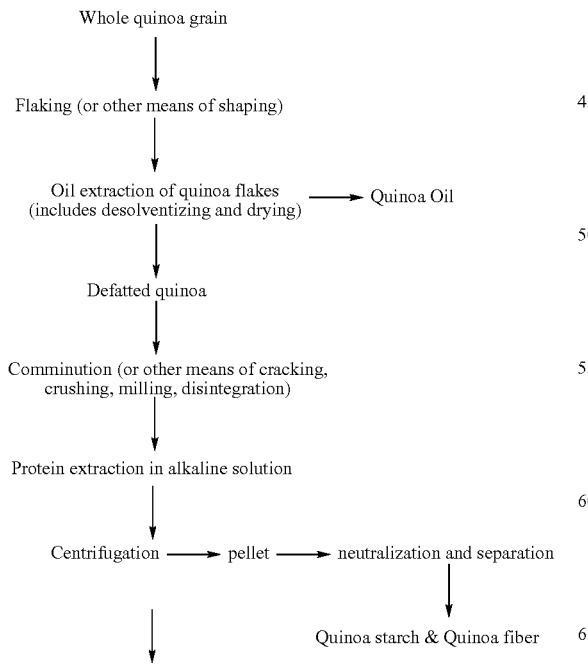

Scheme 1. Preparation of quinoa protein concentrate from *Chenopodium quinoa*, Chenopodiaceae

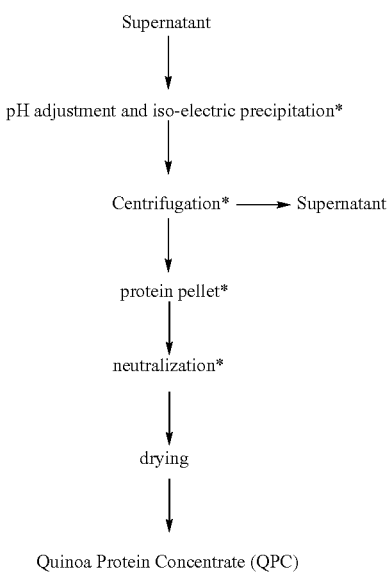

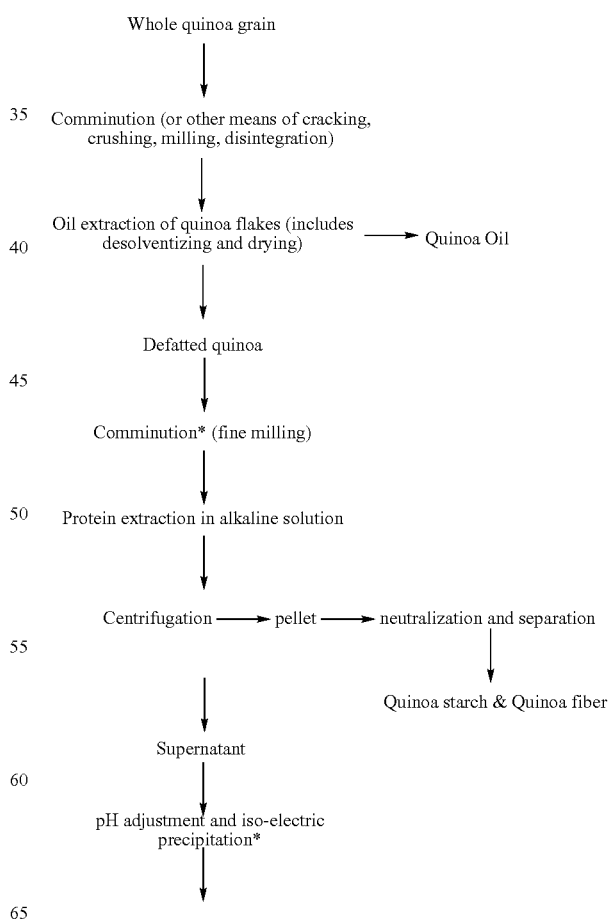

Scheme 2. Preparation of quinoa protein concentrate from *Chenopodium quinoa*, Chenopodiaceae

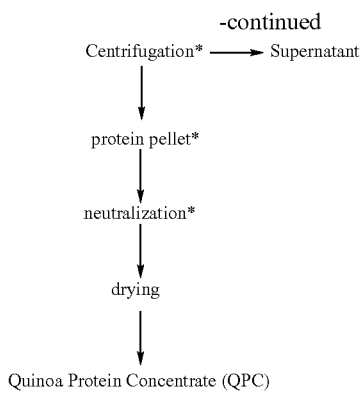

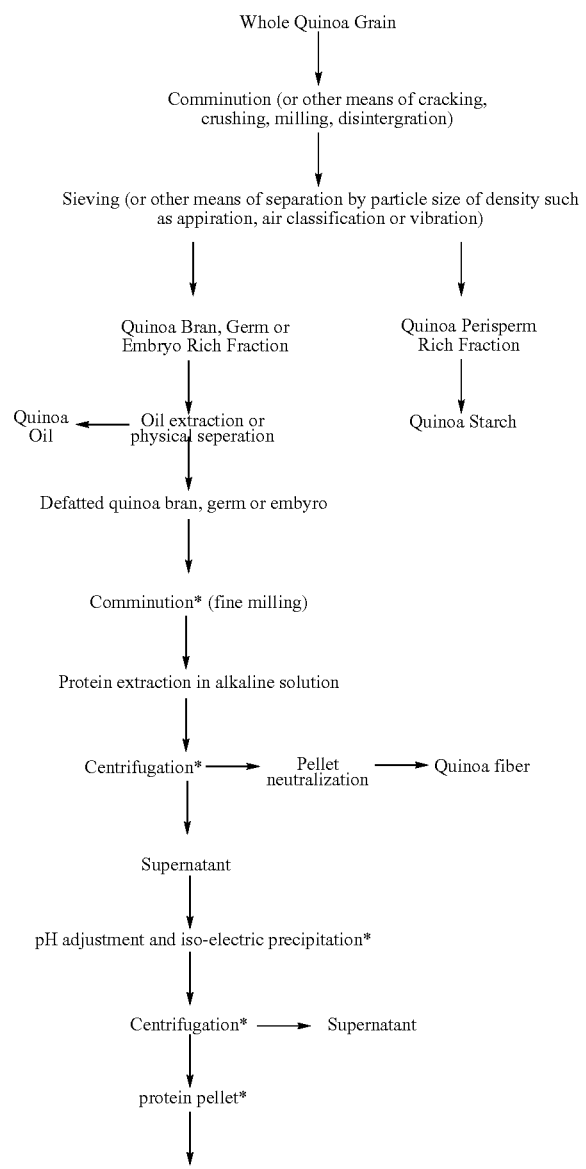

Scheme 3. Preparation of quinoa protein concentrate from *Chenopodium quinoa*, Chenopodiaceae The process provides means to isolate individual components of nutritional and commercial value from *quinoa* grain, all of which are food- and pharmaceutical-grade. For example, *quinoa* oil which is present at about 6-9% in unprocessed quinoa seed can be obtained at a level above 80% from the initial solvent extraction or mechanical extraction (e.g., cold pressing or expeller pressing). Likewise, the starch level obtained from the process is above 80%. *Quinoa* fiber isolated from the process is at a level of at least 50%. The steps indicated with * are optional in isolating *quinoa* protein concentrate, i.e., one can obtain *quinoa* protein concentrate in the range of at least about 50% on a dry weight basis without carrying out the steps indicated. Accordingly, the present invention provides a *quinoa* protein concentrate having at least about 50 wt %, specifically at least about 55 wt %, at least about 60 wt %, at least about 65 wt %, at least about 70 wt %, at least about 75 wt %, at least about 80 wt %, at least about 85 wt %, at least about 90 wt %, at least about 95 wt %, or 99 wt % on a dry weight basis.

QPC isolated by the process can be used instead of or in combination with other plant proteins such as alfalfa proteins, grass proteins, soya proteins and rape proteins, etc., or animal proteins such as milk proteins and meat proteins in pet food and animal feed. QPC can also be used in processed foods, diet foods, health food or nutritional supplements, gluten free products, and as a substitute for wheat and other grains, milk, and eggs. QPC is also useful for nutritional purposes as a source of high quality protein in a wide variety of high-energy food and beverage products (protein bars, protein drinks, nutritional beverages including meal replacement (drinks).

QPC may be used in conventional applications of protein concentrates, such as, protein fortification of processed foods, emulsification of oils, body formers in baked goods and foaming agents in products which entrap gas. QPC would also be used for a variety of functional effects that are associated with proteins, e.g., as a gelation aid in yogurts and pudding, as a water binder in meat and sausage, as a foaming or whipping aid in toppings and fillings, and as an emulsifier in ice cream, margarine, and mayonnaise. In addition, QPC may be formed into protein fibers, useful in meat analogs, and may be used as an egg white substitute or extender in food products where egg white is used as a binder. Other uses of QPC are in edible films and capsules, biodegradable packaging, industrial and cosmetic applications, and in personal care products. QPC can replace all or a portion of the fat or cream in food products such as ice cream, yogurt, salad dressing, mayonnaise, cream, cream cheese, other cheeses, sour cream, sauces, icings, whipped toppings, frozen confections, milk, coffee whitener and spreads. QPC can be hydrolyzed to produce a variety of vegetarian flavors as in the case with hydrolyzed vegetable proteins from soy.

Sample Preparation:

*Quinoa* grain was harvested and cleaned with sieves and shaking belts to remove stems, rocks, and debris, similar to the manner by which other grains are cleaned prior to processing. Optionally, *quinoa* can further be mechanically abraded, similar to rice polishing, to remove the outer pericarp (or hull) before the next step below.

Fat Extraction:

Whole *quinoa* grain was flaked, similar to oat flakes, at ambient temperature, using flaker (Series No. 2188 size 18×12 HD, Ross Machine & Mill Supply, Oklahoma City, Okla.) with a roll gap of 0.051 mm, or similar art-known flaking equipment, with or without tempering to adjust the moisture content of the grain to achieve optimum results. Alternatively, whole *quinoa* grain may be comminuted (ground, cracked, crushed or milled, etc.) or a combination thereof, with or without tempering to adjust the moisture content of the grain to achieve optimum results. *Quinoa* oil was extracted from *quinoa* flakes with 1:1 w/v (quinoa:ethanol) using lab Model IV oil extractor, size 0.25 cu ft (Crown Iron Works, Roseville, Minn.). *Quinoa* oil was extracted from *quinoa* flakes on a larger scale, using industry equipment, with 1:1 w/v (*quinoa*:ethanol) using Model IV oil extractor, size 1.9 cu ft (Crown Iron Works, Roseville, Minn.). *Quinoa* oil can be extracted from *quinoa* flakes (as in Scheme 1), comminuted *quinoa* (as in Scheme 2), or bran, germ or embryo rich fractions (as in Scheme 3) using similar art-known oil extraction equipment. Other nonpolar solvents, such as hexane, methanol, acetone, and isopropyl alcohol, can also be used to extract oil. This step of defatting can be carried out at later steps, for example, after concentrating and drying the protein, if desired. Other methods of defatting can be used including supercritical liquid $CO_2$ extraction and mechanical pressing. The preferred ratio of *quinoa* to solvent is about 1:1 (w/v) and residence time in the extractor is 60 min, however, this ratio and residence time can be adjusted depending on the solvent and a given sample of *quinoa*. *Quinoa* oil micelle and solvent mixture was separated from the *quinoa* marque (the defatted material containing protein, starch, fiber etc.) using the oil extractor equipment. The solvent was recovered from the *quinoa* oil and the *quinoa* marque was desolventized and dried with mild heat, to prevent or minimize damage to protein and starch, using Down Draft Desolventizer-Toaster-Dryer-Cooler (Crown Iron Works, Roseville, Minn.). Solvent can be recovered from *quinoa* oil and *quinoa* marque using similar art-known oil desolventizer equipment. The oil was refined further by physical and/or caustic refining, similar to corn and soybean oil refining. Desolventizing and drying *quinoa* marque removes moisture and residual solvent and what is left is called defatted *quinoa*.

Protein Extraction:

Ten grams of defatted *quinoa* was milled finely to about 100 microns or less, using a Lab Micro Mill, to yield defatted *quinoa* flour (also called oil seed meal). To extract protein, the defatted *quinoa* flour was suspended in 100 ml of 0.03 mol/l sodium hydroxide (any food grade base can be used) and stirred mechanically at ambient temperature for about 4 hours to maximize solubility of the protein. The pH of the suspension is about 10. The suspension mixture was centrifuged for 30 minutes at 6,000 g at about 0-10° C. using a lab centrifuge. The supernatant ("super 1") containing protein was separated from the pellet ("pellet 1") containing fiber, starch, and insoluble protein. *Quinoa* protein was extracted from defatted *quinoa* flour on a larger scale, using industry equipment. Defatted *quinoa* was milled finely to about 100 microns or less, using a Pin Mill, to yield defatted *quinoa* flour. To extract protein, the defatted *quinoa* flour was suspended in 0.03 mol/l sodium hydroxide and stirred mechanically at ambient temperature ranging from 2 to 5.5 hours to maximize solubility of the protein. The suspension mixture was centrifuged for 30 seconds at 3,500 g at ambient temperature using a decanter centrifuge and centrifuged for 60 seconds at 7,000 g at ambient temperature using a disc stack centrifuge. The supernatant ("super 1") containing protein was separated from the pellet ("pellet 1") containing fiber, starch, and insoluble protein. This separation can also be achieved using similar centrifuge equipment or hydrocyclone separators that are well known in the art. Alternatively, *quinoa* protein can be extracted from *quinoa* bran, germ or embryo rich fractions (as in Scheme 3).

The optimal ratio of the defatted *quinoa* flour to alkaline solution is 1:10 (w/v), however, this ratio can be adjusted, if necessary, and the molarity of the alkaline solution and defatted *quinoa* flour suspension can be adjusted to obtain a pH in the range of 8-12. The temperature is not critical for this step and can be readily modified. The length of the extraction should be adjusted to maximize protein recovery, in our hands, about 4 hours yielded most protein.

The pH of the super 1 was then adjusted to about 4.25 with hydrochloric acid (any food grade acidulant can be used) in order to precipitate the protein. The pH for this step can be in the range of 3-6.5. The pellet containing protein precipitates was separated by centrifugation. On a lab scale, the protein precipitates were centrifuged for 30 minutes at 13,000 g at about 0-10° C. The newly obtained pellet ("pellet 2") can be used as a protein source as it is at this stage. Generally, the protein pellet is resuspended in a small volume of water (e.g., 1 g/10 ml $H_2O$), neutralized (~pH 7) and freeze-dried. Alternatively, the protein precipitates were settled, the supernatant ("super 2") was decanted, and the settled protein was neutralized (~pH 7) and freeze-dried. On a larger scale, using industry equipment, the protein precipitates were centrifuged for 60 seconds at 7,000 g at ambient temperature using a disc stack centrifuge. The newly obtained pellet ("pellet 2") can be used as a protein source as it is at this stage, however, the pellet was neutralized (~pH 7) and spray-dried.

Alternatively, the protein does not have to be precipitate. The pH of the super 1 can be adjusted in the range of about 6 to 8, preferably about 7.0. *Quinoa* protein can be prepared from this neutralized protein fraction simply by drying or dewatering the protein using filtration followed by drying the protein.

The protein pellet can be separated using other means such as hydroclone separators or simply by letting the protein settle over time.

The product obtained at this stage typically contains about 90 wt % protein, on a dry weight basis, as determined by micro-Kjeldahl method or Dumas combustion method [American Association of Cereal Chemists: "Approved Methods of Analysis," The Association, St. Paul, Minn., 2000]. Depending on the exact procedure used to obtain the protein concentrate from *quinoa* (referred herein as "*quinoa* protein concentrate"), the protein content ranges from about 50 wt % to at least about 90 wt %.

Starch and Fiber Extraction:

The pellet 1 obtained as above was resuspended in 100 ml of water on a lab scale. The suspension was neutralized and vacuum filtered through a series of wire mesh cloths, with select mesh sizes, in order to separate the starch from the material such as fiber and insoluble proteins. Alternatively, the pH of the suspension was adjusted to about 5.5 (the range for cellulase activity is 3 to 7) and the temperature was increased to about 50° C. (the range of cellulase activity is 25-70° C.). Carbohydrases, specifically cellulases, enzymes that catalyze the breakdown of cell walls, into glucose, cellobiose and higher glucose polymers, were added to the suspension. The pH and the temperature were maintained during the enzyme digestion for about 1 hour. The digest was neutralized and vacuum filtered through a series of wire mesh cloths in order to separate the starch from the partially digested fiber and insoluble proteins. The digestion step using cellulases improves the yield of *quinoa* starch. On a larger scale, using industry equipment, pellet 1 was resuspended in water, neutralized and sieved through a series of screens, with select mesh sizes, using a vibratory separator. This step can be carried out by equipment, such as cyclones, that are known in the art. The separated starch was spray dried. The separated fiber was spray dried. Alternatively, *quinoa* starch can be extracted from perisperm rich fractions and *quinoa* fiber can be extracted from *quinoa* bran, germ or embryo rich fractions (as in Scheme 3). A Buhler Mill was used to separate the bran, germ or embryo rich fractions from the perisperm rich fraction.

*Quinoa* Oil:

*Quinoa* has potential to be a greater and more nutritional source of oil than oil produced from cereals crops (Fleming and Galwey 1995 supra). The oil content of *quinoa* is about 5.6%, with some varieties having lipid contents up to 9.5%. The yield of extractable vegetable oil per hectare could easily exceed that obtained from maize (80-400 kg/ha and 20-50 kg/ha, *quinoa* and maize, respectively) making *quinoa* a valuable new oil crop [Koziol (1990) In: Wahli, ed. Quinua: Hacia su Cultivo Comercial. Latinreco S A, Casilla, 17-110-6053. Quito, Ecuador, ppg. 137-159]. *Quinoa* oil is rich in unsaturated fatty acids. Although desirable nutritionally, unsaturated fatty acids are unstable to oxidation. However, *quinoa* oil is quite stable due to high levels of natural antioxidant vitamin E, 690-740 ppm α-tocopherol and 790-930 ppm γ-tocopherol. Although Koziol found concentrations fall to 450 and 230 ppm, respectively, after refining, 100-200 ppm is sufficient for optimal antioxidant activity of these isomers [Hudson and Ghavami (1984) *Lebensm Wiss U Technol.* 72: ppg. 82-85].

High lipid content compared with traditional cereals and essential fatty acid profile make *quinoa* a potential valuable oil crop. *Quinoa* oil is a rich source of essential fatty acids linoleic and linolenic, which constitute approximately 55-63% of the oil [Ruales and Nair (1993) *Food Chemistry* 48(2): ppg. 131-136; Fleming and Galwey (1995) supra], and make it similar to that of soya oil. In a comparison of fatty acids and triacylglycerol compositions, *quinoa* oil had the lowest saturate/unsaturate ratio compared with oils from five Amaranthus accessions, buckwheat, corn, ricebran, sesame, soybean and cottonseed [Jahaniaval, F et al. (2000) *JAOCS* 77(8): ppg. 847-852]. In addition, *quinoa* and soybean oils had the most favorable linoleic to linolenic acid ratio of the preceding oils.

Starch and Other Carbohydrates:

Studies on the physico-chemical characteristics of *quinoa* starch have been carried out by Wolf, M J et al. (1950) *Cereal Chem.* 27: ppg. 219-222; Scarpati de Briceño and Biceño (1982) In: Tercer Congreso Internacional de Cultivos Andinos. Ministerio de Asuntos Campesinos y Agropecuarios La Paz, Bolivia. 8-12(2): ppg. 69-77; Atwell, W A et al. (1983) *Cereal Chem.* 60(1): ppg. 9-11; Varriano-Marston and deFrancisco A (1984) *Food Microstructure* 3: ppg. 165-173; and Lorenz (1990) *Starch/Stärk* 42(3): ppg. 81-86. The size of the starch granule and its amylose content are important factors in determining functional properties in food systems. Starch granules occur in the perisperm cells as compound granular aggregates and the individual starch granule is small and uniform with an average particle size of 1-2 μm [Atwell, et al (1983) supra], compared with that of maize and wheat, 1-23 μm and 2-40 μm respectively (Wolf, et al (1950) supra; Swinkels, J J M (1985) In: Van Beynum G M A and Roels J A, eds. Starch Conversion Technology. Dekker, N.Y. ppg. 15-46]. Although small starch granules have been shown to have reduced baking potential [Kulp, K (1973) *Cereal Chem.* 50: ppg. 666-679], the small size and uniformity of *quinoa* starch granules impart a smooth texture and mouthfeel. This attribute has gained considerable interest from food, paper, and cosmetic industries. Consequently, in 1989 European Patent Application No 89121654.1 was established for the manufacture of a carbohydrate-based cream substitute from *quinoa* starch. Small *quinoa* starch granules also have application as inexpensive filler in low density polyethylene films [Ahamed, N T et al. (1996) *Carbohydrate Polymers* 31(3): ppg. 157-160].

Atwell, et al (1982) supra performed an in-depth characterization of *quinoa* starch. Analysis indicates 11% amylose content, which is low in comparison to most cereal starches. It is comparable, however, to some varieties of rice, as reported by Williams, V R et al. (1958) *J. Aric. Food Chem.* 6: pg. 47. Lorenz (1990) supra, found that *quinoa* starch performs poorly in cake and bread baking due to its low amylose content and small starch granule. The researcher also found a higher swelling power of *quinoa* starch than that of barley, wheat, rice, amaranth, and potato, thus performing well as a thickening agent in fillings.

Free sugars in *quinoa* were evaluated to contain 4.55%, 2.41%, and 2.39%, glucose, fructose, and sucrose, respectively [González, J A et al. (1989) *Plant Foods for Human Nutr.* 39: ppg. 331-337]. In the same study, the starch level was much lower than that reported by other authors [Ranhotra, G S et al. (1993) *Cereal Chem.* 70(3): ppg. 303-305]. Consequently, due to high enzyme activity, starch levels will decrease and free sugars will increase upon grinding into flour.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

All references cited in the present application are incorporated in their entirety herein by reference to the extent not inconsistent herewith.

We claim:

1. A *quinoa* fruit protein concentrate having a protein content of at least about 50 wt % on a dry weight basis.

2. The *quinoa* fruit protein concentrate of claim 1 wherein said protein content is at least about 70 wt % on a dry weight basis.

3. The *quinoa* fruit protein concentrate of claim 1 wherein said protein content is at least about 90 wt % on a dry weight basis.

4. The *quinoa* fruit protein concentrate of claim 1 which is in dry powdered form.

5. A method of processing *quinoa* fruit comprising the steps of:

comminuting or milling the *quinoa* fruit;

separating the embryo-rich fraction from the perisperm-rich fraction of the comminuted *quinoa* fruit;

extracting the oil from the embryo-rich fraction of the comminuted *quinoa* fruit to produce defatted *quinoa;* extracting the protein from the defatted *quinoa* using an alkaline solution to solubilize the protein in the defatted *quinoa;* separating solubilized protein in the alkaline solution from the insoluble fiber of the defatted *quinoa*; and drying the separated protein, whereby a *quinoa* protein concentrate containing at least about 50 wt % protein is obtained.

6. The method of claim 5 further comprising a step of purifying the protein by isoelectric precipitation at a pH of about 3.0 to about 6.5 after the step of separating solubilized protein but before the step of drying the separated protein.

7. The method of claim 5 wherein the pH of the resulting alkaline solution having the solubilized protein is in the range of about 8.0-12.0.

8. The method of claim 5 wherein the oil extraction is carried out by a nonpolar solvent or a mechanical process.

9. The method according to claim 5 wherein the step of separating the embryo-rich fraction from the perisperm-rich fraction of the comminuted *quinoa* fruit is performed by a technique selected from the group consisting of sieving, aspiration, air classification and vibration.

10. The method according to claim 5 further comprising the step of collecting the perisperm-rich fraction resulting from the step of separating the embryo-rich fraction from the perisperm-rich fraction of the comminuted *quinoa* fruit, whereby a *quinoa* starch product is obtained.

11. The method according to claim 5 further comprising the step of collecting the extracted *quinoa* oil from the oil extraction step, whereby a *quinoa* oil product is obtained.

12. The method according to claim 5 further comprising the steps of:

collecting the insoluble fiber from the protein separation step; and neutralizing the collected fiber, whereby a *quinoa* fiber product is obtained.

13. The method according to claim 5 further comprising the step of neutralizing the separated protein prior to the drying step.

14. The method according to claim 5 further comprising the steps of:

precipitating the separated protein;

isolating the precipitated protein from the supernatant; and neutralizing the precipitated protein prior to the drying step.

15. A method of processing *quinoa* fruit comprising the steps of:

milling the *quinoa* fruit;

extracting the oil from the flaked *quinoa* leaving defatted *quinoa;* collecting the extracted *quinoa* oil, whereby a *quinoa* oil product is obtained;

comminuting the defatted *quinoa;* extracting the protein from the defatted *quinoa* using an alkaline solution to solubilize the protein in the defatted *quinoa;* separating solubilized protein from the insoluble fiber of the defatted *quinoa*; and drying the separated protein, whereby a *quinoa* protein concentrate containing at least about 50 wt % protein is obtained.

16. The method according to claim 15 further comprising the step of:

neutralizing the separated fiber, whereby a *quinoa* starch and fiber product is obtained; and separating the *quinoa* starch from the *quinoa* fiber in the *quinoa* starch and fiber product.

17. The method according to claim 15 further comprising the step of neutralizing the separated protein prior to the drying step.

18. The method according to claim 15 further comprising the steps of:

precipitating the separated protein;

isolating the precipitated protein from the supernatant; and neutralizing the isolated protein prior to the drying step.

* * * * *